United States Patent
West et al.

(10) Patent No.: US 6,391,554 B1
(45) Date of Patent: *May 21, 2002

(54) DETECTING CANCEROUS CONDITIONS BY ASSAYING FOR TELOMERASE ACTIVITY

(75) Inventors: Michael D. West, Boston, MA (US); Jerry W. Shay; Woodring E. Wright, both of Dallas, TX (US); Nam Woo Kim, San Jose, CA (US); Calvin B. Harley, Palo Alto, CA (US); Scott L. Weinrich, Redwood City, CA (US)

(73) Assignees: Geron Corporation and Board of Regents, Menlo Park, CA (US); The University of Texas Systems, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/447,151

(22) Filed: Nov. 23, 1999

Related U.S. Application Data

(63) Continuation of application No. 08/255,774, filed on Jun. 7, 1994, now Pat. No. 5,989,807, which is a continuation-in-part of application No. 08/151,477, filed on Nov. 12, 1993, now Pat. No. 5,830,644, and a continuation-in-part of application No. 08/153,051, filed on Nov. 12, 1993, now Pat. No. 5,645,986, which is a continuation-in-part of application No. 08/060,952, filed on May 13, 1993, now Pat. No. 5,695,932, which is a continuation-in-part of application No. 08/038,766, filed on Mar. 24, 1993, now Pat. No. 5,489,508, which is a continuation-in-part of application No. 07/882,438, filed on May 13, 1992, now abandoned.

(51) Int. Cl.[7] .............................. C12Q 1/68; C12Q 1/48; C12Q 19/34; G01N 33/53
(52) U.S. Cl. .......................... 435/6; 435/15; 435/91.2; 435/7.2
(58) Field of Search .............................. 435/6, 15, 91.2, 435/7.2; 536/24.31, 24.33; 436/64

(56) References Cited

U.S. PATENT DOCUMENTS

| 4,737,454 A | 4/1988 | Dattagupta et al. | 435/6 |
| 5,489,508 A | 2/1996 | West et al. | 435/6 |
| 5,645,986 A | 7/1997 | West et al. | 435/6 |
| 5,830,644 A | 11/1998 | West et al. | 435/6 |
| 5,989,807 A | 11/1999 | West et al. | 435/6 |

FOREIGN PATENT DOCUMENTS

| WO | 93/04546 | 11/1993 |
| WO | 94/08053 | 4/1994 |

OTHER PUBLICATIONS

S. Wang and V Zakian. "Telomere–telomere recombination provides an express pathway for telomere acquisition" *Nature* 345:456 (1990).

(List continued on next page.)

*Primary Examiner*—Carla J. Myers
(74) *Attorney, Agent, or Firm*—Lyon & Lyon LLP

(57) ABSTRACT

Methods and kits are provided for diagnosis of specific cancerous conditions. The invention features a method for diagnosis of a condition in a patient associated with an elevated level of telomerase activity within a cell. The method involves determining the presence or amount of telomerase within the cells in the patient, e.g. by the use of the polymerase chain reaction. In one embodiment of the invention, the condition associated with elevated telomerase activity is chosen from prostate cancer, breast cancer, colon cancer, renal cancer, ovarian/cervical cancer, lung cancer, and leukemia. The invention allows cancer to be detected even in tissues and cells which are not positive by pathology.

5 Claims, 12 Drawing Sheets

Telomerase Activity in Prostatic Tissues and Cells

| Diagnosis | No. positive/ No. tested |
|---|---|
| Normal prostate tissue | 0/6 |
| Benign prostatic hyperplasia (BPH) | 1/10 |
| Prostatic intraepithelial neoplasia | 3/5 |
| Adenocarcinoma (adjacent section positive) | 2/2 |
| Bladder/prostate cell lines | 3/3 |

OTHER PUBLICATIONS

S. Goldstein "Replicative senescence: the human fibroblast comes of age" *Science* 249:1129. (1990).

J. Smith and R. Whitney. "Intraclonal variation in proliferative potential of human diploid fibroblasts:stochastic mechanisms for cellular aging." *Science* 207:82 (1980).

T. Ohno. "Strict relationship between dialyzed serum concentration and cellular life span in vitro." *Mechanisms of aging and development* 11:179 (1979).

L. Hayflick and P. Moorhead "The serial cultivation of human diploid cell strains." *Experimental Cell Research* 25:585. (1961).

J. Szostak. "The beginning of the ends." *Nature* 337:303 (1989).

G. Jankovic, et al. "Telomere loss and cancer." *Nature* 350:197. (1991).

J. Gall. "Tying up loose ends" *Nature* 344:108 (1990).

G. Yu, et al.. "In vivo alteration of telomere sequences and senescence caused by mutated Tetrahymena telomerase RNAs" *Nature* 344:126. (1990).

L. Harrington and C. Greider "Telomerase primer specificity and chromosome healing" *Nature* 353:451. (1991).

J. Gray, et al.. "Cloning an dexpression of genes for the Oxytricha telomere–binding proteinspecific subunit interactions in the telomereic complex." *Cell* 67:807 (1991).

F. Muller, et al. "New telomere formation after developmentally regulated chromosomal breakage during the process of chromosome diminution in *Ascaris lumbricoides.*" *Cell* 67:815. (1991).

G. Yu and E. Blackburn. "Developmentally programmed healing of chromosomes by telomerase in Tetrahymena." *Cell* 67:823 (1991).

E. Blackburn, et al.. "Recognition and elongation of telomeres by telomerase." *Genome* 31:553 (1989).

C. Greider "Telomeres, telomerase and senesence." *Bioessays* 12:363. (1990).

E. Henderson, et al. "Telomere G–strand structure and function analyzed by chemical protection, base analogue substitution, and utilization by telomerase in vitro." *Biochemistry* 29:732. (1990).

D. Gottschling, et al. Position effect at *S. cerevisiae* telomeres: reversible repression of Pol II transcription. *Cell* 63:751. (1990).

V. Lundblad and J. Szostak "A mutant with a defect in telomere elongation leads to senescence in yeast." *Cell* 57:633. (1989).

E. Blackburn "The molecular structure of centromeres and telomeres." *Annual Reviews in Biochemistry* 53:163. (1984).

A. Olovnikov "A theory of marginotomy." *J. Theoretical Biology* 41:181. (1973).

E. Blackburn. "Structure and function of telomeres." *Nature* 350:569 (1991).

H. Cooke and B. Smith "Variability at the telomeres of the human X/Y pseudoautosomal region" *CSHSQB* LI:213. (1986).

C. Greieder. "Chromosome first aid." *Cell* 67:645 (1991).

G. Morin "The human telomere terminal transferase enzyme is a ribonucloprotein that synthesizes TTAGGG repeats." *Cell* 59:521. (1989).

C. Harley, et al.. "Telomerers shorten during ageing of human fibroblasts" *Nature* 345:458 (1990).

Ham and McKeehan. "Media and growth requirements" (1979) *Methods in Enzymology* LVIII:44.

J. Starling, et al.. "Extensive telomere repeat arrays in mouse are hypervariable" *Nucleic Acids Research* 18:6881 (1990).

Greider and Blackburn, "The Telomere Terminal Transferase of Tetrahymena is a Ribonucleoprotein Enzyme with two kinds of Primer Specificity", 51 *Cell* 887, 1987.

Blackburn et al., "Recognition and elongation of telomeres by telomerase", 31 *Genome* 553, 1989.

Grieder, "Telomerase is Processive", 11 *Molec. and Cell. Biology* 4572, 1991.

Counter et al., "Telomere shortening associated with chromosome instability is arrested in immortal cells which express telomerase activity", 11 *EMBO* 1921, 1992.

Harley, "Telomere loss: mitotic clock or genetic time bomb?", 256 *Mutation Res.* 271, 1991.

Eck and Nabel, "Antisense oligonucleotides for therapeutic intervention", 2 *Opin. Biotech* 897, 1991.

Zahler et al., "Inhibition of telomerase by G–quartet DNA structures", 350 *Nature,* 718, 1991.

Yu and Blackburn "Developmentally Programmed Healing of Chromosomes by Telomerase in Tetrahymena", 67 *Cell* 823, 1991.

Harley et al., "Telomeres shorten during ageing of human fibroblasts", 345 *Nature* 458, 1990.

Blackburn, "Structure and function of telomeres", 350 *Nature* 569, 1991.

Cech, "Ribozymes and Their Medical Implications", 260 *JAMA* 3030, 1988.

Greider and Blackburn, "A telomeric sequence in the RNA of Tetrahymena telomerase required for telomere repeat synthesis," *Nature* 337:331–337 (1989).

Cotton, "The in vivo application of ribozymes," *Trends in Biotechnology* 8:174–178 (1990).

Harley et al., "The Telomere Hypothesis of Cellular Aging," *Experimental Gerontology* 27:375–382 (1992).

Shay et al., "Loss of telomeric DNA during aging may predipose cells to cancer (Review)," *Int'l J. Oncology* 3:559–563 (1993).

Windle and McGuire, "Telomeres: the long and the short of it," *Proceedings of the American Association for Cancer Research* 33:594–595 91992).

Counter et al., "Stabilization of Short Telomeres and Telomerase Activity Accompany Immortalization of Epstein_Barr Virus–Transformed Human B Lymphocites," *J. Virology* 68:3410–3414 (1994).

Klingelhutz et al., "Restoration of Telomeres in Human Papoillomavirus–Immortalized Human Anogenital Epithelial Cells," *Molecular and Cellular Biology* 14:961–969 (1994).

Counter et al., "Telomerase activity in human ovarian carcinoma," *Proc. National Acad. Sci. USA* 91:2900–2904 (1994).

Strahl and Blackburn, "The effects of nucleoside analogs on telomerase and telomeres in Tetrahymena," *Nucleic Acids Research* 22:893–900 (1994).

| Normal/Premalignant Primary Human Tissues | Presence of Telomerase Activity |
|---|---|
| 1. placenta | 0/1 |
| 2. normal prostate<br>   benign prostatic hyperplastic tissue<br>   prostatic intraepithelial neoplasia (PIN3) | 0/6<br>1/10<br>3/5 |
| 3. breast tissue<br>   (from reduction or augmentation mammmoplasty)<br><br>"normal" breast tissue from breast cancer patients<br>   (positive axillary lymph nodes) | 0/8<br><br><br>2/17<br>(one low/one high activity) |
| 4. kidney (from Wilm's tumor patient) | 2/6<br>(both low activity) |
| 5. upper airway (adjacent to squamous cell carcinoma) | 4/7<br>(3 low and one high activity) |
| 6. normal cadaver tissues (12 hours postmortem)<br>   (duodenum, liver, kidney, spleen, brain, prostate, muscle) | |
| 7. testis (12 hours postmortem, 3 hours rt, 9 hrs 4 °C)<br>   testis (12 hours + 18 hours temperature)<br>   testis (12 hours + 18 hours rt + 44 hr 4 °C) | |
| 8. normal colon (from cancer patient)<br>   polyp<br>   tubular adenoma<br>   Duke's 2A colon carcinoma 1.5 hrs postoperative<br>   Duke's 2B colon carcinoma 1.5 hrs postoperative<br>   Duke's 2B colon carcinoma 1.5 hrs postop + 5 hr 4 °C<br>   Duke's 2B colon carcinoma 1.5 hrs postop + 18 hr 4 °C<br>   Duke's 2B colon carcinoma 1.5 hrs postop + 66 hr 4 °C | |

Telomerase Activity in Prostate Tissues

| Diagnosis | Adjacent Section Pathology | No. positive/ No. tested |
|---|---|---|
| Prostate cancer (1%, 10%) | normal | 0/2 |
| Prostate cancer (30%) | normal | 0/1 |
| Prostate cancer | normal | 5/7 |
| Prostate cancer (20%, 25%) | BPH | 1/3 |
| Prostate cancer (60% + PIN) | BPH | 1/1 |
| Prostate cancer | BPH + PIN | 1/1 |
| Prostate cancer | cancer | 2/2 |

FIG. 3.
Telomerase Activity in Prostatic Tissues and Cells

| Diagnosis | No. positive/ No. tested |
|---|---|
| Normal prostate tissue | 0/6 |
| Benign prostatic hyperplasia (BPH) | 1/10 |
| Prostatic intraepithelial neoplasia | 3/5 |
| Adenocarcinoma (adjacent section positive) | 2/2 |
| Bladder/prostate cell lines | 3/3 |

FIG. 4.
Telomerase Activity in Breast Tissues and Cells

| Diagnosis | No. positive/No. tested |
|---|---|
| Normal breast tissue & cells | 0/14 |
| Breast cancer | 17/22 |
| Primary carcinoma (axillary node negative) | 1/4 |
| Low grade phylloides tumor | 1/1 |
| Lobular adenocarcinoma (node positive) | 1/2 |
| (adjacent "normal" tissue) | (0/2) |
| Ductal adenocarcinoma | 14/15 |
| (adjacent "normal" tissue) | (2/15) |
| Metastatic adenocarcinoma (node) | 1/1 |
| Breast carcinoma cell lines | 22/22 |

FIG. 6.
Telomerase Activity in Human Tumors

| Tumor tissue | No. positive/No. tested |
|---|---|
| Squamous cell carcinoma<br>head & neck | 7/7 |
| Hematologic malignancies<br>lymphoma 4, chronic lymphocytic leukemia 2 | 6/6 |
| Wilm's tumor | 6/6 |
| Neuroblastoma | 3/3 |
| Gastrointestinal malignancies<br>hepatoma, Dukes B colon cancer | 2/2 |
| Miscellaneous<br>lung adenocarcinoma 2, rhabdomyosarcoma 1 | 3/3 |

FIG. 7
Absence of Telomerase Activity in Normal Cells

| Cell Line | No. positive/No. tested |
|---|---|
| Fibroblasts lung PDL30&35, foreskin PDL55, synovial PDL9 | 0/4 |
| Breast epithelial cells HME PDL20-41 | 0/5 |
| Breast stromal cells | 0/3 |
| Epithelial cells cervical & endometrial | 0/2 |
| Fetal aminocytes | 0/15 |
| Miscellaneous umbilical endothelial, skin keratinocyte | 0/2 |

FIG. 8.
Telomerase Activity in Cell Lines

| Cell Line | No. positive/No. tested |
|---|---|
| Renal carcinoma | 3/3 |
| Bladder/prostate carcinoma | 3/3 |
| Ovarian/cervical carcinoma | 3/3 |
| Breast carcinoma | 7/7 |
| Colon carcinoma | 2/2 |
| Lung carcinoma | 8/8 |
| Leukemia/lymphoma | 5/5 |
| Miscellaneous<br>fibrosarcoma 1, CNS carcinoma 3, melanoma 2 | 6/6 |

Detection of Telomerase Activity Using PCR-based Assay

FIG. 10

Telomerase activity in extract extends oligonucleotide primer M2 by stepwise addition of 6 nt (TTAGGG)

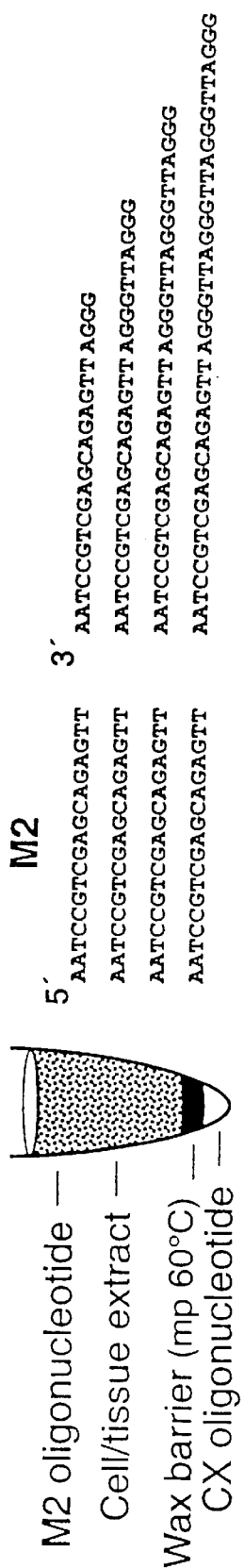

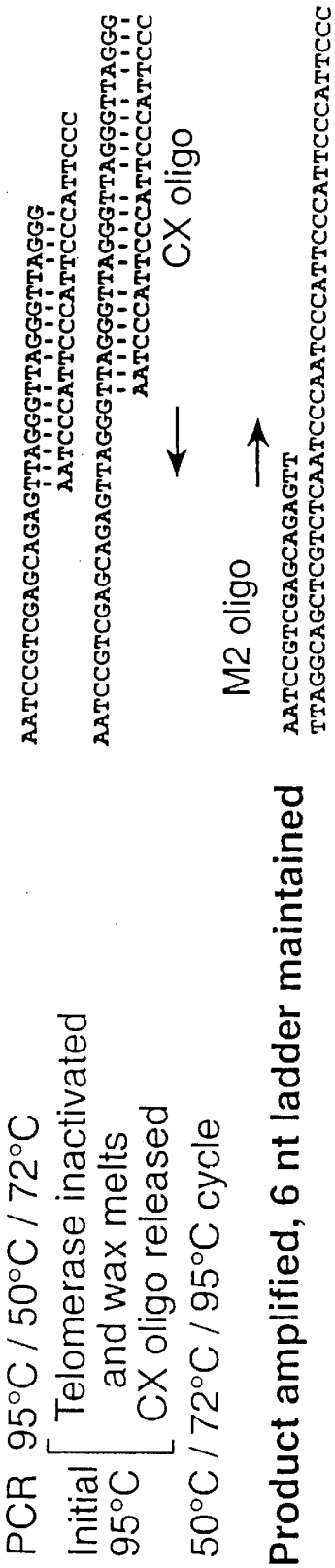

Amplification: Telomerase-extended M2 oligonucleotide amplified by PCR

PCR 95°C / 50°C / 72°C

Initial 95°C [ Telomerase inactivated and wax melts
CX oligo released

50°C / 72°C / 95°C cycle

Product amplified, 6 nt ladder maintained

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
      (A) LENGTH: 24
      (B) TYPE: nucleic acid
      (C) STRANDEDNESS: sin gle
      (D) TOPOLOGY: linear (ii) SEQUENCE DESCRIPTION: SEQ ID NO: 1:

CCCTTACCCT TACCCTTACC CTAA          24

(2) INFORMATION FOR SEQ ID NO: 2:

(i) SEQUENCE CHARACTERISTICS:
      (A) LENGTH: 18
      (B) TYPE: nucleic acid
      (C) STRANDEDNESS: sin gle
      (D) TOPOLOGY: linear (ii) SEQUENCE DESCRIPTION: SEQ ID NO: 2:

AATCCGTCGA GCAGAGTT          18

(2) INFORMATION FOR SEQ ID NO: 3:

(i) SEQUENCE CHARACTERISTICS:
      (A) LENGTH: 24
      (B) TYPE: nucleic acid
      (C) STRANDEDNESS: sin gle (D) TOPOLOGY:  linear (ii) SEQUENCE DESCRIPTION: SEQ ID NO: 3:

CCCTTACCCT TACCCTTACC CTTA                                           24

(2) INFORMATION FOR SEQ ID NO:    4:

(i) SEQUENCE CHARACTERISTICS:
        (A) LENGTH:  24
        (B) TYPE:  nucleic acid
        (C) STRANDEDNESS:  sin gle
        (D) TOPOLOGY:  linear (ii) SEQUENCE DESCRIPTION: SEQ ID NO: 4:

GCGCGGCTAA CCCTAACCCT AACC                                           24

(2) INFORMATION FOR SEQ ID NO:    5:

(i) SEQUENCE CHARACTERISTICS:
        (A) LENGTH:  21
        (B) TYPE:  nucleic acid
        (C) STRANDEDNESS:  sin gle
        (D) TOPOLOGY:  linear (ii) SEQUENCE DESCRIPTION: SEQ ID NO: 5:

CTAACCCTAA CCCTAACTCT G                                              21

(2) INFORMATION FOR SEQ ID NO:    6:

(i) SEQUENCE CHARACTERISTICS:
        (A) LENGTH:  23
        (B) TYPE:  nucleic acid
        (C) STRANDEDNESS:  sin gle
        (D) TOPOLOGY:  linear (ii) SEQUENCE DESCRIPTION: SEQ ID NO: 6:

CCCAATCCGT CGAGCAGAGT TAG                                            23

(2) INFORMATION FOR SEQ ID NO:    7:

(i) SEQUENCE CHARACTERISTICS:
        (A) LENGTH:  22
        (B) TYPE:  nucleic acid
        (C) STRANDEDNESS:  sin gle
        (D) TOPOLOGY:  linear (ii) SEQUENCE DESCRIPTION: SEQ ID NO: 7:

TAACTCTGCT CGACGGATTC CC                                             22

(2) INFORMATION FOR SEQ ID NO:    8:

(i) SEQUENCE CHARACTERISTICS:
        (A) LENGTH:  21
        (B) TYPE:  nucleic acid
        (C) STRANDEDNESS:  sin gle
        (D) TOPOLOGY:  linear (ii) SEQUENCE DESCRIPTION: SEQ ID NO: 8:

GGGTAACCCT AACCCTAACC C                                              21

(2) INFORMATION FOR SEQ ID NO:    9:

(i) SEQUENCE CHARACTERISTICS:
        (A) LENGTH:  19
        (B) TYPE:  nucleic acid

```
        (C) STRANDEDNESS:  sin gle
        (D) TOPOLOGY:  linear (ii) SEQUENCE DESCRIPTION: SEQ ID NO: 9:

GGTTAGGGTT AGGGTTAAA                                                    19
```

DETECTING CANCEROUS CONDITIONS BY ASSAYING FOR TELOMERASE ACTIVITY

This application is a continuation of U.S. Ser. No. 08/255,774, filed Jun. 7, 1994, now U.S. Pat. No. 5,989,807, which is a continuation-in-part of U.S. Ser. No. 08/151,477, filed Nov. 12, 1993, now U.S. Pat. No. 5,830,644, and a continuation-in-part of U.S. Ser. No. 08/153,051, filed Nov. 12, 1993, now U.S. Pat. No. 5,645,986, both of which are continuations-in-part of U.S. Ser. No. 08/060,952, filed May 13, 1993, now U.S. Pat. No. 5,695,932, which is a continuation-in-part of U.S. Ser. No. 08/038,766, filed Mar. 24, 1993, now U.S. Pat. No. 5,489,508, which is a continuation-in-part of application Ser. No. 07/882,438, filed May 13, 1992, now abandoned.

BACKGROUND OF THE INVENTION

This invention relates to methods for diagnosis of cellular senescence and immortalization.

The following is a general description of art relevant to the present invention. None is admitted to be prior art to the invention.

Michael D. West et al., entitled "Therapy and Diagnosis of Conditions Related to Telomere Length and/or Telomerase Activity," U.S. application Ser. No. 08/151,477, filed Nov. 12, 1993, and PCT WO 93/04546 filed Nov. 25, 1993, both hereby incorporated by reference, generally describe art which relates to cellular senescence, and theories or hypotheses which explain such aging and the mechanisms by which cells escape senescence and immortalize. West et al. discusses the use of telomerase activity detection for diagnosis of various cancerous conditions.

West et al., U.S. application Ser. No. 08/151,477, filed Nov. 12, 1993, describes methods by which telomerase activity can be used to determine whether a cell is immortalized. One such method (example 21) involves providing appropriate primers and using the polymerase chain reaction to determine the presence of telomerase activity in the cells.

In this method, West et al. rely upon the ability of telomerase to template and catalyze the synthesis of telomeric sequence onto a single-stranded oligodeoxynucleotide (oligo) substrate. The conventional assay for this activity uses an oligo of known sequence as substrate, radioactive deoxynucleotide triphosphate (DNTP) for labeling, and sequencing gel for resolution and display of the products. Since telomerase stalls and can release the DNA after adding the first G in the $T_2AG_3$ repeat, the characteristic pattern of products is a six nucleotide ladder of extended oligo substrate. The phase of the repeats depends on the 3' end sequence of the oligo substrate; telomerase recognizes where it is in the repeat and synthesizes accordingly to yield contiguous repeat sequence. Although telomeric sequence oligos are the most efficient in vitro substrates, telomerase will also synthesize $T_2AG_3$ repeats onto non-telomeric oligos.

The basis of the assay of West et al. is application of the polymerase chain reaction (PCR) for specific amplification of the in vitro products of telomerase. The telomerase reaction portion of the assay is unchanged. The telomerase products (the nested set of one to hundreds of six nucleotide telomeric repeats added to the oligo substrate) serve as the templates for PCR amplification. Exponential amplification is achieved by a PCR primer set consisting of a downstream primer complementary to telomeric repeats and an upstream primer composed of sequence from the oligo substrate. In fact, the oligo substrate (typically an 18-mer) itself serves as the upstream primer and since a standard telomerase reaction contains 1 $\mu$M oligo substrate of which less than 1% is extended by telomerase, there is no need to add more for the PCR reaction. A downstream primer of comparable length is used. A stringent annealing temperature in the PCR cycle ensures specific primer binding which results in preservation of the six nucleotide ladder in the PCR products, reflective of the template population.

West et al. determined a downstream primer which they designated CX. CX is composed of sequence complementary to three imperfect telomeric repeats and one perfect repeat (5'(CCCTTA)$_3$CCCTAA-3') (SEQ. ID No. 1). The single nucleotide difference in three of the repeats compromises the capacity of CX to anneal to the 3' end of M2 (which contains 5 of 6 nucleotides of a telomeric repeat). Under optimized conditions, West et al. found that M2 and CX alone in a PCR reaction set up at room temperature and then subjected to 27 cycles of 95°, 50°, and 72° produced no PCR products.

As yet another measure to prevent primer interaction and non-specific amplification, West et al. also suggested that the hot start method be utilized. In this technique, CX was dried at the bottom of the tube and then covered with a wax barrier. All other PCR reaction components were combined in the tube above the wax barrier, and the tube was placed in the thermal cycler. With this set-up, CX did not appear in the PCR reaction until the wax melted (about 60° C.) during the first cycle, preventing CX interaction with any other reaction component at a temperature below the annealing temperature.

West et al. suggested that since both telomerase and Taq polymerase are DNA synthesizing enzymes with similar reaction components, the assay could be further streamlined by combining the activities in a single reaction. A single tube protocol was achieved. In this protocol, CX oligo is isolated by wax barrier for hot start of the PCR. All other reaction components are combined above the wax barrier including the telomerase oligo substrate/upstream primer M2, the telomerase extract, and Taq polymerase. PCR buffer and deoxynucleotide conditions allow sufficient telomerase product generation in 10 minutes at room temperature. The tubes are then simply placed in the thermal cycler for PCR. West et al. showed that specific amplification of telomerase products under these conditions occurs if and only if the oligo substrate M2 has been extended with three or more $T_2AG_3$ repeats.

West et al. also determined that a correlation exists between telomerase activity and the tumor cell phenotype.

SUMMARY OF THE INVENTION

The present invention is directed to methods and kits for diagnosis of specific cancerous conditions, e.g by using the polymerase chain reaction to determine telomerase activity.

Thus, in a first aspect, the invention features a method for diagnosis of a condition in a patient associated with an elevated level of telomerase activity within a cell. The method involves determining the presence or amount of telomerase activity within the cells in the patient, wherein the condition associated with elevated telomerase activity is chosen from prostate cancer, breast cancer, colon cancer, renal cancer, ovarian/cervical cancer, lung cancer, and leukemia.

In a second aspect, the method involves determining the presence or amount of telomerase activity within the cells by the use of the polymerase chain reaction. The improved sensitivity of the PCR-based assay allows the detection of telomerase activity in tumor tissue, which was not reliable using the conventional published assay.

In a related aspect, the method involves determining the presence or amount of telomerase activity for the detection of cancers, of any type, including solid tumors and leukemias (including those in which cells are immortalized, including: apudoma, choristoma, branchioma, malignant carcinoid syndrome, carcinoid heart disease, carcinoma (e.g., Walker, basal cell, basosquamous, Brown-Pearce, ductal, Ehrlich tumor, in situ, Krebs 2, merkel cell, mucinous, non-small cell lung, oat cell, papillary, scirrhous, bronchiolar, bronchogenic, squamous cell, and transitional cell), histiocytic disorders, leukemia (e.g., b-cell, mixed-cell, null-cell, T-cell, T-cell chronic, HTLV-II-associated, lyphocytic acute, lymphocytic chronic, mast-cell, and myeloid), histiocytosis malignant, Hodgkin's disease, immunoproliferative small, non-Hodgkin's lymphoma, plasmacytoma, reticuloendotheliosis, melanoma, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, Ewing's sarcoma, synovioma, adenofibroma, adenolymphoma, carcinosarcoma, chordoma, craniopharyngioma, dysgerminoma, hamartoma, mesenchymoma, mesonephroma, myosarcoma, ameloblastoma, cementoma, odontoma, teratoma, thymoma, trophoblastic tumor, adenocarcinoma, adenoma, cholangioma, cholesteatoma, cylindroma, cystadenocarcinoma, cystadenoma, granulosa cell tumor, gynandroblastoma, hepatoma, hidradenoma, islet cell tumor, leydig cell tumor, papilloma, sertoli cell tumor, theca cell tumor, leiomyoma, leiomyosarcoma, myoblastoma, myoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinosarcoma, chondrosarcoma, cystosarcoma phyllodes, fibrosarcoma, hemangiosarcoma, leiomyosarcoma, leukosarcoma, liposarcoma, lymphangiosarcoma, myosarcoma, myxosarcoma, ovarian carcinoma, rhabdomyosarcoma, sarcoma (e.g., Ewing's, experimental, Kaposi's, and mast-cell), neoplasms (e.g., bone, breast, digestive system, colorectal, liver, pancreatic, pituitary, testicular, orbital, head and neck, central nervous system, acoustic, pelvic, respiratory tract, and urogenital), neurofibromatosis, and cervical dysplasia), and for treatment of other conditions in which cells have become immortalized.

By "elevated level" of telomerase activity it is meant that the absolute level of telomerase activity in the particular cell is elevated compared to normal cells in that individual, or compared to normal cells in other individuals not suffering from the condition. Generally, any detectable level of telomerase activity is considered elevated in this invention, as exemplified below. That is, in a human tissue, except for germ cells and stem cells, telomerase activity is generally not detectable. Germ and stem cells can be distinguished from other cell types which exhibit telomerase activity using methods known to those skilled in the art. Applicant has determined that the detection of telomerase activity is indicative not only of the presence of known cancer cells, but also of precancerous cells. By precancerous cells, it is meant that the cells would be classified as non-cancerous by pathology. Thus, the method of the instant invention allows cancerous conditions to be detected before cells become visibly cancerous.

The method of the present invention provides the advantage of allowing cancer to be detected in all tissue types by the use of telomerase as a marker. In addition, we have surprisingly found that cancer can be detected in cells which are shown to be normal by pathology, and have used the method of the present invention to detect cancer in several tissue samples.

In a further aspect, the invention comprises a kit for performing the above method. Such a kit may be prepared from readily available materials and reagents.

DESCRIPTION OF THE PREFERRED EMBODIMENTS

The drawings will first be briefly described.

FIGS. 1–8 depict the results of the telomerase activity assay in various tissues and cells.

FIG. 10 depicts an assay for telomerase activity using the polymerase chain reaction. Specifically, a one tube PCR-based telomerase assay is shown. The figure shows the extension of the M2 primer by addition of telomere repeat sequences (TTAGGG) by telomerase activity in cell extract, and shows the PCR amplification of the extended M2 oligonucleotide.

Figure 11:
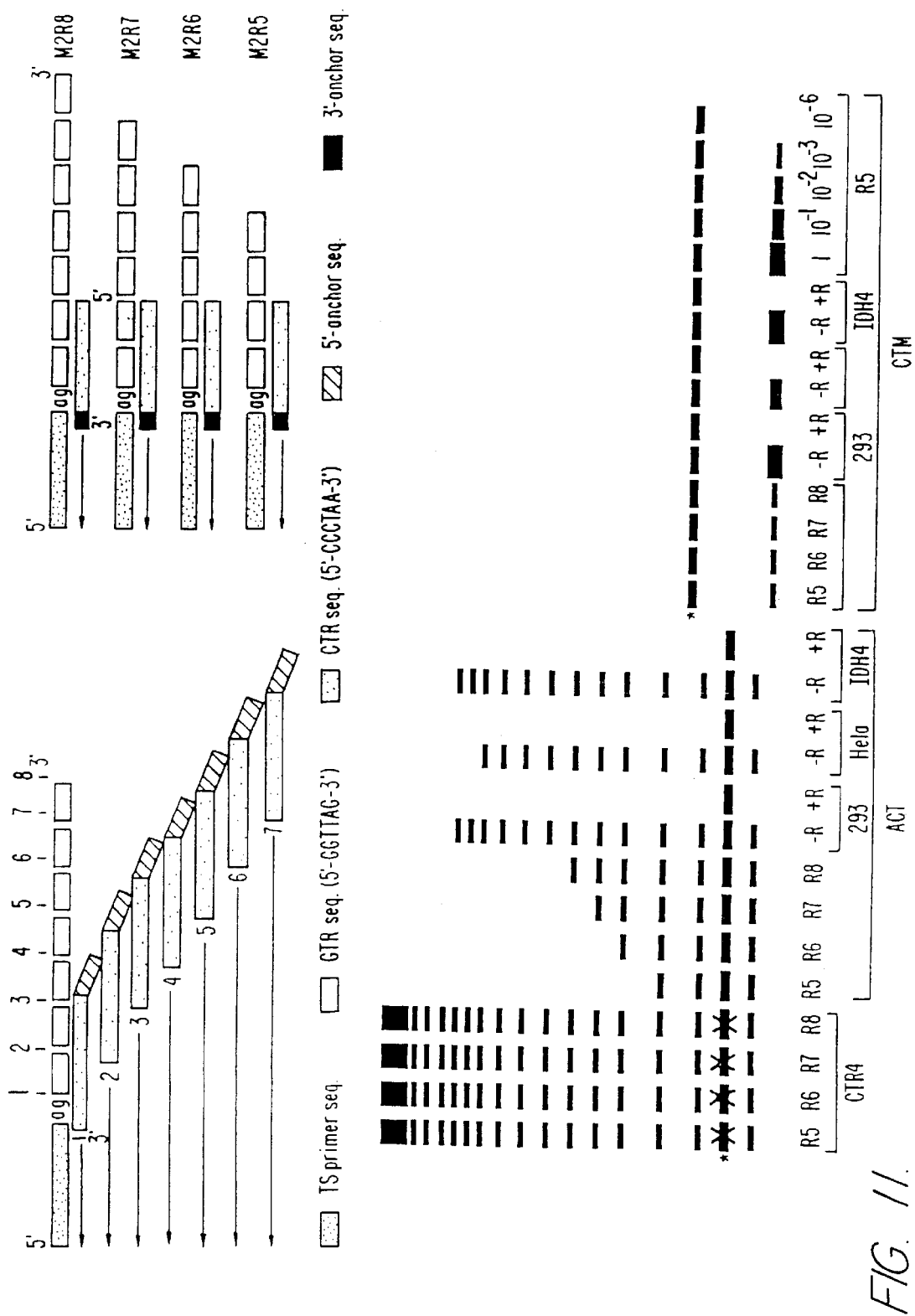

FIG. 11 depicts an improvement of the polymerase chain reaction assay for telomerase activity.

METHODS

The methods of the present invention are generally described above. Below are non-limiting examples depicting these methods.

The method of the present invention was used to detect telomerase activity in various tissues and cells using the specific conditions and protocols described below. The results are given in FIGS. 1–5.

FIG. 1 depicts the results of several assays for telomerase activity. This figure shows that telomerase activity can occasionally be detected in cells which are not cancerous by pathology, e.g., benign prostatic hyperplastic tissue, and the "normal" breast tissue adjacent to tumor tissue from breast cancer patients. Thus, this method can be used to help determine whether the entire breast or prostate should be removed, or if less invasive procedures might be adequate.

FIG. 2 depicts the detection of telomerase activity in prostate tissue using a method of the instant invention. The first column shows the diagnosis by pathology of the whole tissue sample from which the original diagnosis was made, and gives the percentage of cancerous cells contained in that sample. The second column shows the diagnosis by pathology of the cells actually used in the instant assay. The third column shows the results of the instant assay. This FIG. shows that some cells which were normal by pathology tested positive for telomerase activity.

FIG. 3 depicts the detection of telomerase activity in prostate tissue using a method of the instant invention. The "normal" prostate tissue in this figure was from young patients, who were unlikely to have prostate cancer, and exhibited no evidence of prostate cancer. One individual without cancer but with BPH was telomerase positive. Three out of five samples diagnosed with prostate intraepithelial neoplasia, and two out of two diagnosed with adenocarcinoma were positive, as were three out of three tumor cell limes from the urinary system.

FIG. 4 depicts the detection of telomerase activity in breast tissues using a method of the instant invention. This figure shows that telomerase activity was not detected in normal breast epithelial cells in culture, or in normal breast tissue. However, telomerase activity was detected in cells which appeared to be normal, e.g., the normal tissue adjacent to ductal adenocarcinoma, and in various types of tumors. Telomerase activity was detected in 22 out of 22 breast tumor cell lines.

Figure 5:
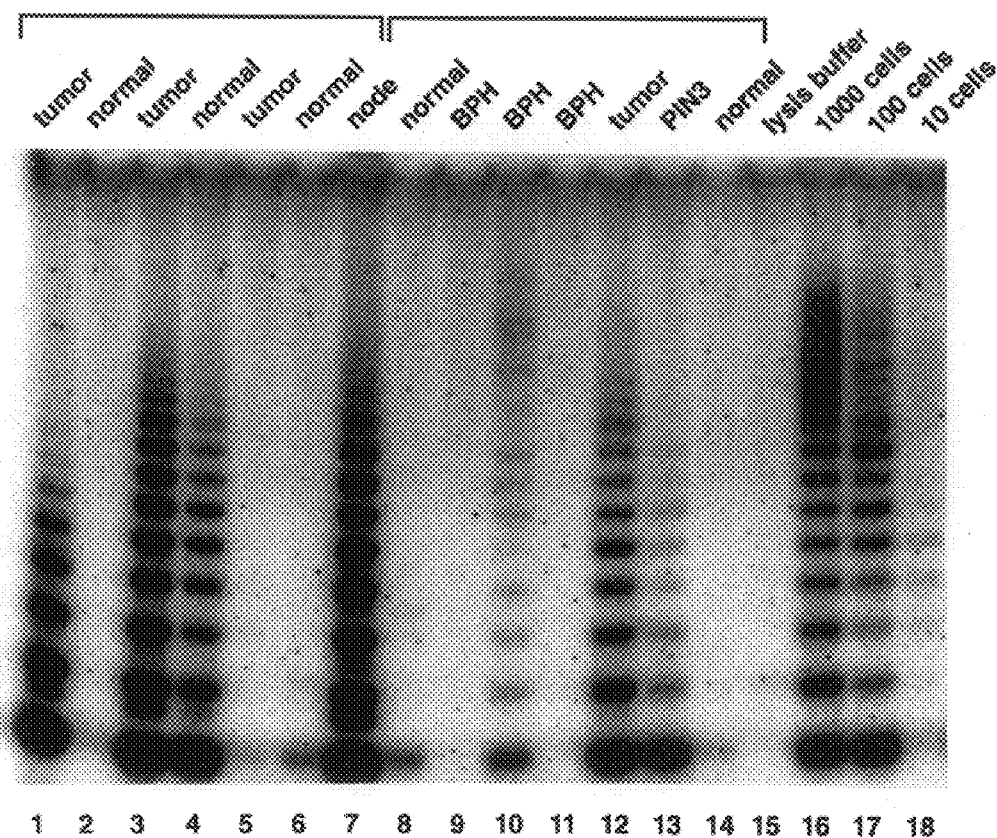
Figure 9A:
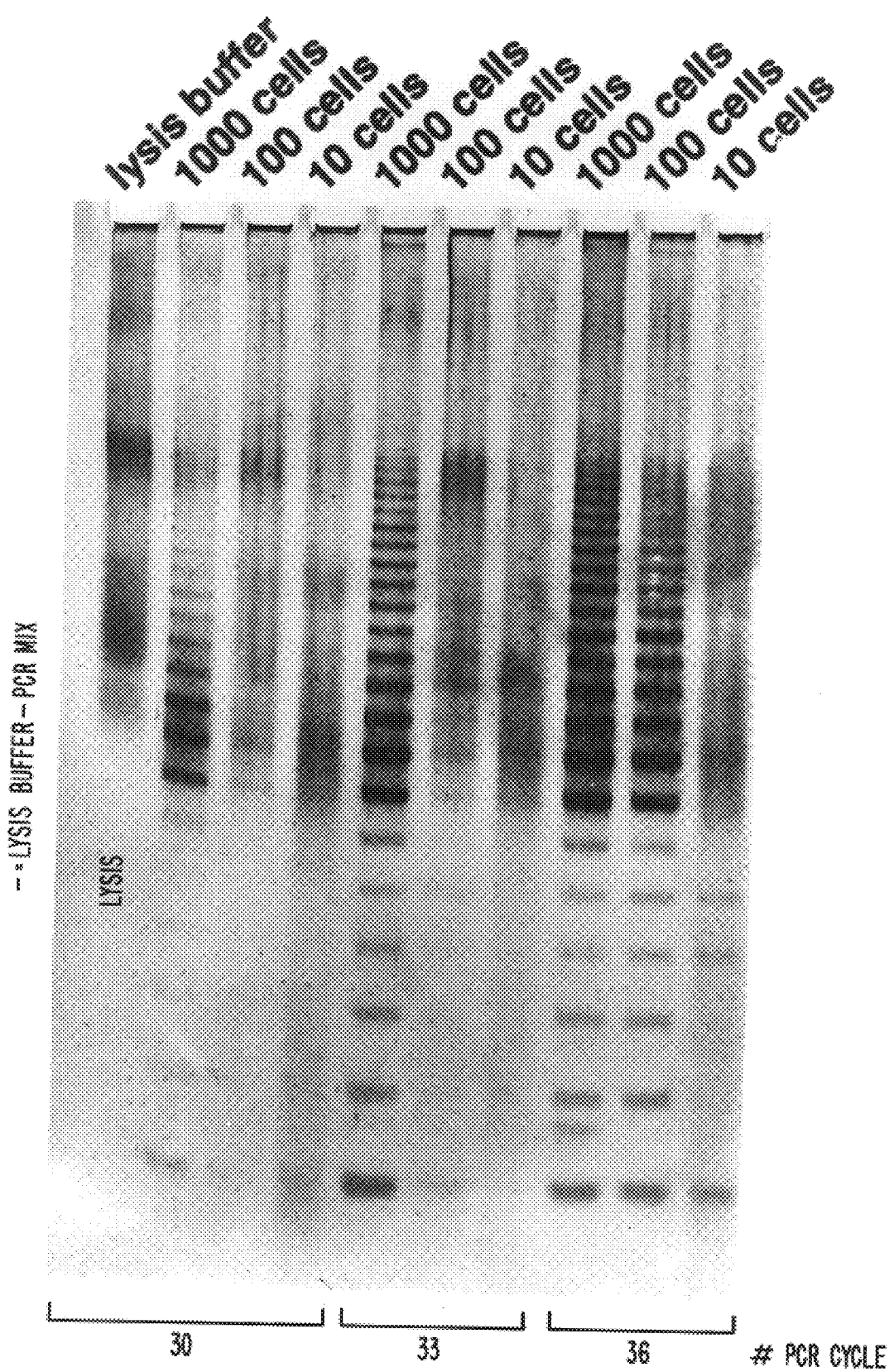
FIG. 9 depicts the increase in sensitivity of the assay with the increase in number of cycles of the polymerase chain reaction.
Figure 9B:
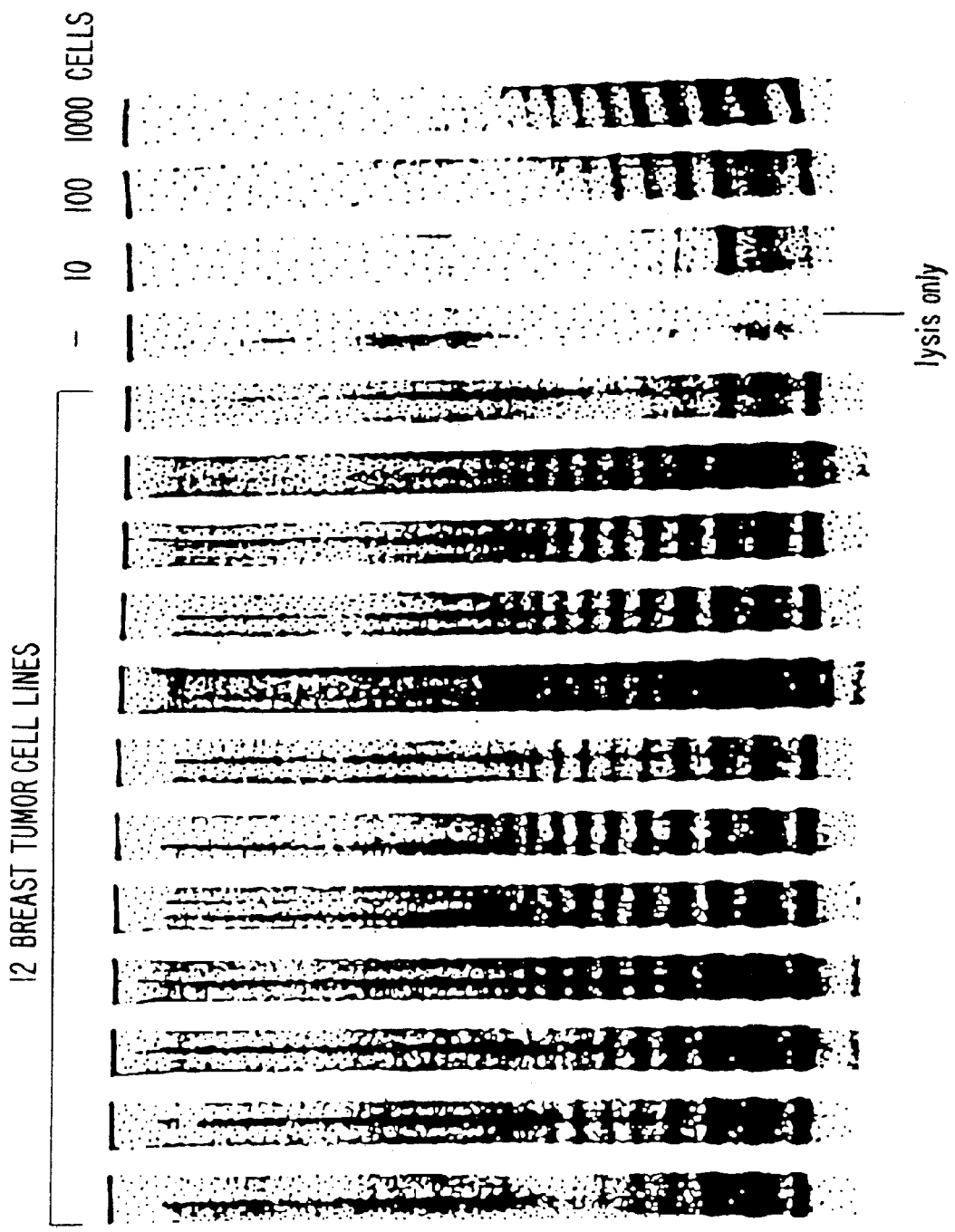

FIG. 5 is a copy of an autoradiogram showing the results of the above assays in breast and prostate tissues. While normal breast tissue generally displayed no telomerase activity (lanes 2 and 6), tumor tissue was generally positive for activity (lanes 1 and 3). In lane 4, a sample of breast tissue adjacent to the tumor shown in lane 3 is assayed. This adjacent sample was judged to be univolved by the pathologist. In lane 7 a lymph node from a breast cancer patient is shown to have telomerase activity. In the case of prostate tissue, generally tissue from benign prostatic hypertrophy is negative for telomerase activity. Lane 10 shows one sample out of ten was positive.

FIGS. 6–8 depict the detection of telomerase assay in various cell lines using the method of the instant invention.

EXAMPLES

The following are examples of specific aspects of the invention to merely illustrate this invention to those in the art. These examples are not limiting of the invention, but provide an indication of specific methodology useful in practice of the invention. They also provide clear indication of the utility of the invention.

Example 1

Assay for Telomerase Activity in Cells and Tissues

The following specific conditions and protocols were used to detect telomerase activity in tissue and cell samples.
Materials
  Washing Buffer:
    10 mM HEPES-KOH, pH 7.5; 1.5 mM $MgCl_2$; 10 mM KCl;
  DEPC water; 1 mM DTT;
  Lysis Buffer:
    10 mM Tris-HCl, pH 7.5; 1 mM $MgCl_2$; 1 mM EGTA; 0.5% CHAPS; 10% Glycerol; DEPC water; 5 mM BME; 0.1 mM PMSF;
  Reaction Solution:
    DEPC water; 1× T-PCR buffer; 30$\mu$M dNTPs; 344 nM primer M2; 0.5 $\mu$M T4g32prot.; 2 U/assay Taq Pol.; 2 uCI/assay dCTP; 2 uCI/assay dTTP;
Lysis of Cells in Culture
  Pellet 100,000 cells (6,000 RPM in an Eppendorf microfuge/ 6 min) in culture medium. Carefully remove supernatant, put dry pellet in −80° C. immediately.
  Lyse the cells with 200 $\mu$l of ice cold lysis buffer and leave on ice for 30 min. Centrifuge the lysate at 14,000 RPM for 20 min at +4° C.
  Collect 160 $\mu$l of supernatant into an Eppendorf tube making sure that no traces of pellet were withdrawn and flash-freeze in EtOH-dry ice bath. Store at −80° C. Lysate will have extract from 1000 cells/2 $\mu$l.

Extraction of Telomerase from Tissues
  Dispersion of small pieces fresh or flash frozen tissue (100–200 mgs) is done in Kontes tubes with matching pestles.
  Place the tissue (100 mg) in Kontes tube containing 200–250 Al of ice cold lysis buffer. Disperse the tissue with pestle rotating at 450 RPM. Avoid excessive homogenization which may result in overheating the sample, as this could inactivate telomerase.
  Leave the sample on ice for 20 min. Mix occasionally. Centrifuge the lysates at 14,000 RPM for 20 min. at +4° C. Collect ⅔ of supernatant, avoiding any traces of pellet and before flash-freezing the sample in EtOH-dry ice put away the small fraction for protein assay.
Procedure
  Pipette 48 $\mu$l aliquots of reaction solution into PCR tubes containing CX primer overlayed with solidified Ampliwax. Add 2 $\mu$l of telomerase extract/tube and let the telomerase reaction go for 30 min at 20° C. The telomerase reaction conditions can be varied, e.g., 10 min at room temperature can be used. Immediately place the tubes in a PCR heating block prewarmed at 90° C. and run for 30–37 cycles.
  Transfer the reaction mixtures to tubes with 3.3 $\mu$l of 6× Sample Buffer. Load samples on 10% acrylamide gel in 0.5× TBE and run at 175V for 45 min and next increase voltage up to 280V and run until xylene cyanol is 4–6 cm from bottom of gel (1 hr 45 min).
  Samples of several cells lines and tissue types were tested by the above method (see FIG. 1–8). These FIGS. show that the above method allowed cancer to be detected even when the tissue samples were pathologically negative for cancer Specifically, FIGS. 2 and 3 show that the method of this invention detected cancer in prostate tissue which was negative by pathology, and FIG. 4 shows similar results in detecting cancer in breast tissue.
  Another example of possible PCR conditions is as follows. 50 $\mu$l reactions set up at room temperature in the prepared tubes contained 20 mM Tris-HCl pH 8.3; 1.5 mM $MgCl2$; 63 mM KCl; 0.005% Tween 20; 1 mM EGTA; 50 MM DNTPs; 344 nM of M2 ("ITS") oligo (20 pmol, 5'-AATCCGTCGAGCAGAGTT -3') (SEQ. ID. NO. 2); 0.5 mM T4g32prot. (Boeringer Mannheim); 0.1 mg/ml BSA; and, 2U of Taq DNA polymerase (optionally use 2U Taq treated with an equal volume of TaqStart antibody from Clonetech). For radiolabelling of products, 0.2–0.4 ml of 10 mCi/ml 32P-dGTP and/or 32P-dCTP was added to the reaction. The tubes were then transferred to the thermal cycler for 27 rounds of 94° C. for 30 sec., 50° C. for 30 sec., and 72° C. for 1.5 min. One half of the reaction was analyzed by electrophoresis.

Example 2

Use of 5' Anchored Primers to Improve Telomerase Repeat Amplification Protocol The above version of the telomerase repeat amplification protocol (TRAP) has a drawback in that the number of bands on the gel resulting from TRAP analysis do not quantitatively reflect telomeric repeats added by the telomerase in the extract. This phenomenon is caused by a "stagger-binding" effect of CX (5'(CCCTTA)3CCCTAA-3') (SEQ. ID. NO. 1) or CTR4 (5-(CCCTAA)4-3') (SEQ. ID. NO. 3) oligos to the telomerase products in PCR amplification. The use of CTR primer with 6bp "anchor" on the 5' end of the oligo can be used to solve this problem. Primer ACT (5'-GCGCGG(CTAACC)3-3') (SEQ. ID. NO. 4) in conjunction with TS (M2) oligo (5'-AATCCGTCGAGCAGAGTT- 3') (SEQ. ID. NO. 2) produces a ladder pattern that is directly reflective of the number of telomeric repeats on the original telomerase products. This is exemplified in FIG. 11. An added benefit of using ACT oligo is that TS/ACT oligo combination is much more resistant to the formation of primer-dimers, thus less likely to produce false positives.

Example 3

Use of 3'-anchored primers or Ligation Chain Reaction (LRC) to Improve the Quantitative Aspect of TRAP The quantitative aspect of TRAP may be improved by using a CTR primer with few base-pair overlap with TS sequence in its 3' end. One such oligos with this design is CTM (5'CTAACCCTAACCCTAACTCTG-3') (SEQ. ID. NO. 5) which has 7 bp complementary sequences with the last 7 bp of TS on its 3' end. TS/CTM primers should amplify the telomerase products as single-length entities regardless of the number of telomeric repeats, which would simplify the quantitation of telomerase activity by TRAP.

Another method to improve TRAP quantitation is the use of Ligation Chain Reaction (LCR) to amplify the telomerase product. The initial LCR assay would incorporate the following 4 oligonucleotide primers:

LTS (5'-CCCAATCCGTCGAGCAGAGTTAG-3') (SEQ. ID. NO. 6),

CLT (5'-TAACTCTGCTCGACGGATTCCC-3') (SEQ. ID. NO. 7),

LC (5'-GGGTAACCCTAACCCTAACCC-3') (SEQ. ID. NO. 8),

LG (5'-GGTTAGGGTTAGGGTTAAA-3') (SEQ. ID. NO. 9). The use of these oligonucleotide primers maximizes inhibition of the template-independent product formations, but can be utilized to amplify telomerase products. Since the LCR amplification of telomerase products produces an amplified product of identical size, it would improve the quantitative aspect of TRAP.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The present embodiments of this invention are to be considered in all respects as illustrative and not restrictive, the scope of the invention being indicated by the appended claims rather than by the foregoing description, and all changes which come within the meaning and range of equivalency of the claims therefore are intended to be embraced therein.

Other embodiments are within the following claims.

We claim:

1. A method for diagnosis of a condition associated with an elevated level of telomerase activity within mammalian cells comprising:
 determining the presence or amount of telomerase activity within said cells; and
 correlating the presence or amount of telomerase activity with a condition associated with an elevated level of telomerase activity.

2. The method of claim 1, wherein said determining is by template-dependent DNA polymerase chain reaction wherein a primer complementary to telomeres is extended in the presence of telomerase.

3. A method for detection of a cancerous or precancerous condition in a mammal, the method comprising assaying for telomerase activity, wherein a detectable level of telomerase activity is indicative of a cancerous or precancerous condition.

4. The method of claim 1, wherein the condition associated with an elevated level of telomerase activity is cancer.

5. The method of claim 4, wherein the cancer is selected from the group consisting of prostate cancer, breast cancer, colon cancer, renal cancer, ovarian cancer, cervical cancer, leukemia and lung cancer.

* * * * *